(12) United States Patent
Ellison et al.

(10) Patent No.: US 10,047,192 B2
(45) Date of Patent: Aug. 14, 2018

(54) OPTICAL MATERIAL AND ARTICLES FORMED THEREFROM

(71) Applicant: Sirrus, Inc., Loveland, OH (US)

(72) Inventors: Matthew McBrayer Ellison, Mason, OH (US); Bernard Miles Malofsky, Bloomfield, CT (US); Adam Gregg Malofsky, Loveland, OH (US); Tanmoy Dey, Willington, CT (US); Jeffrey M. Sullivan, Goshen, OH (US)

(73) Assignee: Sirrus, Inc., Loveland, OH (US)

( * ) Notice: Subject to any disclaimer, the term of this patent is extended or adjusted under 35 U.S.C. 154(b) by 147 days.

(21) Appl. No.: 14/404,870

(22) PCT Filed: May 31, 2013

(86) PCT No.: PCT/US2013/043711
§ 371 (c)(1),
(2) Date: Dec. 1, 2014

(87) PCT Pub. No.: WO2013/181600
PCT Pub. Date: Dec. 5, 2013

(65) Prior Publication Data
US 2015/0148480 A1 May 28, 2015

Related U.S. Application Data

(60) Provisional application No. 61/693,626, filed on Aug. 27, 2012, provisional application No. 61/654,586, filed on Jun. 1, 2012.

(51) Int. Cl.
*B01F 17/00* (2006.01)
*C08G 63/00* (2006.01)
(Continued)

(52) U.S. Cl.
CPC .............. *C08G 63/00* (2013.01); *C07C 69/38* (2013.01); *C07C 69/708* (2013.01); *C08F 18/14* (2013.01);
(Continued)

(58) Field of Classification Search
CPC ......... C08F 18/14; C08G 63/00; C07C 69/38; C07C 69/708
(Continued)

(56) References Cited

U.S. PATENT DOCUMENTS 2,212,506 A 8/1940 Bachman et al.
2,245,567 A 6/1941 Brant et al.
(Continued)

FOREIGN PATENT DOCUMENTS

CN 102901754 A 1/2013
DE 19508049 A1 9/1996
(Continued)

OTHER PUBLICATIONS

International Search Report (ISR) and Written Opinion of the Searching Authority in App No. PCT/US2016/027134 dated Jul. 15, 2016, 7 pages in its entirety.
(Continued)

*Primary Examiner* — Jane L Stanley
(74) *Attorney, Agent, or Firm* — Ulmer & Berne LLP

(57) ABSTRACT

Optical materials including polymerizable compositions and oligomeric and polymeric material formed therefrom. The oligomer or polymer material include structural repeat units. The optical material has low or substantially no absorbance of wavelengths in at least one of the spectral regions of interest. Optical components include adhesives, waveguides, spherical or non-spherical optical lenses, architectural articles, automotive components, laminated structures and composites.

11 Claims, 5 Drawing Sheets

(51) Int. Cl.
  *C08F 18/14* (2006.01)
  *G02B 1/04* (2006.01)
  *C08F 222/10* (2006.01)
  *C07C 69/38* (2006.01)
  *C07C 69/708* (2006.01)
  *C09J 5/00* (2006.01)
  *C09J 167/00* (2006.01)
  *G02B 6/255* (2006.01)

(52) U.S. Cl.
  CPC .............. *C08F 222/10* (2013.01); *C09J 5/00* (2013.01); *C09J 167/00* (2013.01); *G02B 1/04* (2013.01); *G02B 6/255* (2013.01)

(58) Field of Classification Search
  USPC ........................................................ 524/601
  See application file for complete search history.

(56) References Cited

U.S. PATENT DOCUMENTS

| | | |
|---|---|---|
| 2,277,479 A | 3/1942 | D'Alelio |
| 2,313,501 A | 3/1943 | Bachman et al. |
| 2,330,033 A | 9/1943 | D'Alelio |
| 2,403,791 A | 7/1946 | D'Alelio |
| 2,726,204 A | 12/1955 | Kilbourne et al. |
| 2,730,457 A | 1/1956 | Green et al. |
| 3,042,710 A | 7/1962 | Dickstein et al. |
| 3,140,276 A | 7/1964 | Forster |
| 3,197,318 A | 7/1965 | Halpern et al. |
| 3,203,915 A | 8/1965 | D'Alelio |
| 3,221,745 A | 12/1965 | Coover, Jr. et al. |
| 3,385,777 A | 5/1968 | Haycock et al. |
| 3,427,250 A | 2/1969 | Haas et al. |
| 3,489,663 A | 1/1970 | Bayer et al. |
| 3,523,097 A | 8/1970 | Coover, Jr. et al. |
| 3,557,185 A | 1/1971 | Ito et al. |
| 3,591,676 A | 7/1971 | Hawkins et al. |
| 3,595,869 A | 7/1971 | Shuman |
| 3,677,989 A | 7/1972 | Jenkinson |
| 3,728,373 A | 4/1973 | Imohel et al. |
| 3,758,550 A | 9/1973 | Eck et al. |
| 3,759,797 A | 9/1973 | Masunaga et al. |
| 3,923,836 A | 12/1975 | Bender et al. |
| 3,936,486 A | 2/1976 | Egger et al. |
| 3,940,362 A | 2/1976 | Overhults |
| 3,945,891 A | 3/1976 | Aal et al. |
| 3,966,562 A | 6/1976 | Mukushi et al. |
| 3,975,422 A | 8/1976 | Buck |
| 3,978,422 A | 8/1976 | Rheinfelder |
| 3,995,489 A | 12/1976 | Smith et al. |
| 4,001,345 A | 1/1977 | Gorton et al. |
| 4,004,984 A | 1/1977 | Margen |
| 4,018,656 A | 4/1977 | Rogers et al. |
| 4,035,243 A | 7/1977 | Katz et al. |
| 4,036,985 A | 7/1977 | Amato et al. |
| 4,046,943 A | 9/1977 | Smith et al. |
| 4,049,698 A | 9/1977 | Hawkins et al. |
| 4,056,543 A | 11/1977 | Ponticello |
| 4,079,058 A | 3/1978 | Ackermann et al. |
| 4,080,238 A | 3/1978 | Wolinski et al. |
| 4,083,751 A | 4/1978 | Choi et al. |
| 4,102,809 A | 7/1978 | Smith et al. |
| 4,105,688 A | 8/1978 | Ami et al. |
| 4,118,422 A | 10/1978 | Klein |
| 4,140,584 A | 2/1979 | Margen |
| 4,148,693 A | 4/1979 | Williamson |
| 4,154,914 A | 5/1979 | Kuraya |
| 4,160,864 A | 7/1979 | Ponticello et al. |
| 4,176,012 A | 11/1979 | Bryant |
| 4,186,058 A | 1/1980 | Katz et al. |
| 4,186,060 A | 1/1980 | Katz et al. |
| 4,198,334 A | 4/1980 | Rasberger |
| 4,224,112 A | 9/1980 | Childs |
| 4,229,263 A | 10/1980 | Childs |
| 4,236,975 A | 12/1980 | Childs |
| 4,237,297 A | 12/1980 | Rody et al. |
| 4,243,493 A | 1/1981 | Gruber et al. |
| 4,256,908 A | 3/1981 | Nishimura et al. |
| 4,282,067 A | 8/1981 | Katz et al. |
| 4,282,071 A | 8/1981 | Sherrod |
| 4,291,171 A | 9/1981 | Baum et al. |
| 4,313,865 A | 2/1982 | Teramoto et al. |
| 4,319,964 A | 3/1982 | Katz et al. |
| 4,329,479 A | 5/1982 | Yabutani et al. |
| 4,396,039 A | 8/1983 | Klenk et al. |
| 4,399,300 A | 8/1983 | Prange et al. |
| 4,411,740 A | 10/1983 | Flaningam et al. |
| 4,440,601 A | 4/1984 | Katz et al. |
| 4,440,910 A | 4/1984 | O'Connor |
| 4,443,624 A | 4/1984 | Prange et al. |
| 4,444,928 A | 4/1984 | Karrer |
| 4,450,067 A | 5/1984 | Angevine et al. |
| 4,504,658 A | 3/1985 | Narisada et al. |
| 4,510,273 A | 4/1985 | Miura et al. |
| 4,517,105 A | 5/1985 | Laemmle et al. |
| 4,539,423 A | 9/1985 | Itatani et al. |
| 4,556,649 A | 12/1985 | Salzburg et al. |
| 4,560,723 A | 12/1985 | Millet et al. |
| 4,578,503 A | 3/1986 | Ishikawa et al. |
| 4,584,064 A | 4/1986 | Ciais et al. |
| 4,613,658 A | 9/1986 | Mathias et al. |
| 4,698,333 A | 10/1987 | Fauss et al. |
| 4,720,543 A | 1/1988 | McPherson et al. |
| 4,724,053 A | 2/1988 | Jasne |
| 4,727,801 A | 3/1988 | Yokoi et al. |
| 4,728,701 A | 3/1988 | Jarvis et al. |
| 4,736,056 A | 4/1988 | Smith et al. |
| 4,767,503 A | 8/1988 | Crescentini et al. |
| 4,769,464 A | 9/1988 | Sajtos |
| 4,783,242 A | 11/1988 | Robbins |
| 4,828,882 A | 5/1989 | Tsezos et al. |
| 4,835,153 A | 5/1989 | Kubota et al. |
| 4,840,949 A | 6/1989 | Korbonits et al. |
| 4,897,473 A | 1/1990 | Dombek |
| 4,914,226 A | 4/1990 | Di Trapani et al. |
| 4,931,584 A | 6/1990 | Bru-Magniez et al. |
| 4,932,584 A | 6/1990 | Yamazaki et al. |
| 5,021,486 A | 6/1991 | Galbo |
| 5,039,720 A | 8/1991 | Saatweber et al. |
| 5,064,507 A | 11/1991 | O'Donnell et al. |
| 5,142,098 A | 8/1992 | Bru-Magniez et al. |
| 5,162,545 A | 11/1992 | Etzbach et al. |
| 5,210,222 A | 5/1993 | O'Murchu |
| 5,227,027 A | 7/1993 | Topper |
| 5,259,835 A | 11/1993 | Clark et al. |
| 5,284,987 A | 2/1994 | Sikkenga et al. |
| 5,292,937 A | 3/1994 | Manning et al. |
| 5,312,864 A | 5/1994 | Wenz et al. |
| 5,328,687 A | 7/1994 | Leung et al. |
| 5,334,747 A | 8/1994 | Steffen |
| 5,397,812 A | 3/1995 | Usami et al. |
| 5,426,203 A | 6/1995 | Sohn et al. |
| 5,446,195 A | 8/1995 | Pacifici |
| 5,514,371 A | 5/1996 | Leung et al. |
| 5,514,372 A | 5/1996 | Leung et al. |
| 5,550,172 A | 8/1996 | Regula et al. |
| 5,565,525 A | 10/1996 | Morimoto et al. |
| 5,567,761 A | 10/1996 | Song |
| 5,575,997 A | 11/1996 | Leung et al. |
| 5,582,834 A | 12/1996 | Leung et al. |
| 5,624,669 A | 4/1997 | Leung et al. |
| 5,693,621 A | 12/1997 | Toepfer et al. |
| 5,817,742 A | 10/1998 | Toepfer et al. |
| 5,817,870 A | 10/1998 | Haas et al. |
| 5,886,219 A | 3/1999 | Steffen |
| 5,902,896 A | 5/1999 | Bauer |
| 5,952,407 A | 9/1999 | Rasoul et al. |
| 6,057,402 A | 5/2000 | Zhou et al. |
| 6,069,261 A | 5/2000 | Hoffmann et al. |
| 6,106,807 A | 8/2000 | Albayrak et al. |
| 6,143,352 A | 11/2000 | Clark et al. |
| 6,183,593 B1 | 2/2001 | Narang et al. |
| 6,210,474 B1 | 4/2001 | Romano, Jr. et al. |

(56) References Cited

U.S. PATENT DOCUMENTS

| | | | |
|---|---|---|---|
| 6,211,273 B1 | 4/2001 | Bru-Magniez et al. |
| 6,225,038 B1 | 5/2001 | Smith et al. |
| 6,238,896 B1 | 5/2001 | Ozaki et al. |
| 6,245,933 B1 | 6/2001 | Malofsky et al. |
| 6,284,915 B2 | 9/2001 | Hirase et al. |
| 6,291,703 B1 | 9/2001 | Schaerfl, Jr. et al. |
| 6,376,019 B1 | 4/2002 | Leung |
| 6,395,737 B1 | 5/2002 | Defossa et al. |
| 6,395,931 B1 | 5/2002 | Carvalho et al. |
| 6,413,415 B1 | 7/2002 | Weiss et al. |
| 6,420,468 B2 | 7/2002 | Bru-Magniez et al. |
| 6,440,461 B1 | 8/2002 | Bru-Magniez et al. |
| 6,512,023 B1 | 1/2003 | Malofsky et al. |
| 6,518,677 B1 | 2/2003 | Capote et al. |
| 6,545,097 B2 | 4/2003 | Pinchuk et al. |
| 6,559,264 B1 | 5/2003 | Konig et al. |
| 6,610,078 B1 | 8/2003 | Bru-Magniez et al. |
| 6,613,934 B1 | 9/2003 | Jegelka et al. |
| 6,673,957 B2 | 1/2004 | Bartek et al. |
| 6,699,928 B2 | 3/2004 | Cobbley et al. |
| 6,716,355 B1 | 4/2004 | Hanemaaijer et al. |
| 6,750,298 B1 | 6/2004 | Bru-Magniez et al. |
| 6,794,365 B2 | 9/2004 | Al-Obeidi et al. |
| 6,841,064 B1 | 1/2005 | Weiss et al. |
| 6,936,140 B2 | 8/2005 | Paxton et al. |
| 7,070,675 B2 | 7/2006 | Schmidt et al. |
| 7,109,369 B2 | 9/2006 | Nose et al. |
| 7,169,727 B2 | 1/2007 | Thorman |
| 7,208,621 B2 | 4/2007 | Nose et al. |
| 7,226,957 B1 | 6/2007 | Scranton et al. |
| 7,305,850 B2 | 12/2007 | Tonkovich et al. |
| 7,450,290 B2 | 11/2008 | Xu et al. |
| 7,553,989 B2 | 6/2009 | Sawabe et al. |
| 7,603,889 B2 | 10/2009 | Cypes et al. |
| 7,610,775 B2 | 11/2009 | Tonkovich et al. |
| 7,649,108 B2 | 1/2010 | Schal et al. |
| 7,659,423 B1 | 2/2010 | McArdle |
| 7,663,000 B2 | 2/2010 | Dekkers et al. |
| 7,678,847 B2 | 3/2010 | Yan et al. |
| 7,771,567 B2 | 8/2010 | Rives et al. |
| 7,900,558 B2 | 3/2011 | Yokoi |
| 8,119,214 B2 | 2/2012 | Schwantes et al. |
| 8,206,570 B2 | 6/2012 | Deniau |
| 8,318,060 B2 | 11/2012 | Sundberg et al. |
| 8,425,999 B2 | 4/2013 | McArdle et al. |
| 8,609,885 B2 | 12/2013 | Malofsky et al. |
| 8,884,051 B2 | 11/2014 | Malofsky et al. |
| 9,108,914 B1 | 8/2015 | Malofsky et al. |
| 9,181,365 B2 | 11/2015 | Malofsky et al. |
| 9,217,098 B1 | 12/2015 | Stevenson et al. |
| 9,221,739 B2 | 12/2015 | Malofsky et al. |
| 9,234,107 B2 | 1/2016 | Malofsky et al. |
| 9,334,430 B1 | 5/2016 | Stevenson et al. |
| 9,481,640 B2 | 11/2016 | McArdle et al. |
| 2001/0005572 A1 | 6/2001 | Lobo et al. |
| 2001/0034300 A1 | 10/2001 | Yurugi et al. |
| 2002/0143128 A1 | 10/2002 | Cabioch et al. |
| 2002/0151629 A1 | 10/2002 | Buffkin et al. |
| 2003/0096069 A1 | 5/2003 | D'Alessio |
| 2003/0199655 A1 | 10/2003 | Yurugi et al. |
| 2004/0057914 A1 | 3/2004 | Bonda et al. |
| 2004/0076601 A1 | 4/2004 | Bru-Magniez et al. |
| 2004/0082043 A1 | 4/2004 | Yadav et al. |
| 2004/0086243 A1 | 5/2004 | DiGiovanni et al. |
| 2004/0220060 A1 | 11/2004 | Bartley et al. |
| 2005/0106781 A1 | 5/2005 | Ogata |
| 2006/0001158 A1 | 1/2006 | Matayabas, Jr. et al. |
| 2006/0073334 A1 | 4/2006 | Schwantes et al. |
| 2006/0167267 A1 | 7/2006 | Chorghade et al. |
| 2006/0197236 A1 | 9/2006 | Basheer et al. |
| 2006/0211809 A1 | 9/2006 | Kodemura et al. |
| 2007/0043145 A1 | 2/2007 | Beck et al. |
| 2007/0049655 A1 | 3/2007 | Yoshimune et al. |
| 2007/0092483 A1 | 4/2007 | Pollock |
| 2007/0222051 A1 | 9/2007 | Yoshimura et al. |
| 2008/0131618 A1 | 6/2008 | Nakamura et al. |
| 2008/0160305 A1 | 7/2008 | Warren et al. |
| 2008/0187655 A1 | 8/2008 | Markle et al. |
| 2008/0227919 A9 | 9/2008 | Li et al. |
| 2008/0241485 A1 | 10/2008 | Shimohara et al. |
| 2008/0286333 A1 | 11/2008 | Kangas et al. |
| 2009/0087151 A1 | 4/2009 | Benjamin et al. |
| 2009/0200652 A1 | 8/2009 | Oh et al. |
| 2009/0203861 A1 | 8/2009 | Lee et al. |
| 2009/0263604 A1 | 10/2009 | Arai et al. |
| 2009/0286433 A1 | 11/2009 | Watanabe |
| 2010/0016508 A1 | 1/2010 | Sasagawa et al. |
| 2010/0059179 A1 | 3/2010 | Tribelhorn et al. |
| 2010/0124649 A1 | 5/2010 | Rukavina et al. |
| 2010/0256720 A1 | 10/2010 | Overstreet et al. |
| 2010/0286438 A1 | 11/2010 | Malofsky et al. |
| 2011/0015406 A1 | 1/2011 | Umetani et al. |
| 2011/0024392 A1 | 2/2011 | Sato et al. |
| 2011/0164322 A1 | 7/2011 | Morozumi et al. |
| 2011/0244010 A1 | 10/2011 | Doshi |
| 2011/0255156 A1 | 10/2011 | Jethmalani et al. |
| 2012/0083523 A1 | 4/2012 | Richard et al. |
| 2012/0136130 A1 | 5/2012 | Takashima et al. |
| 2012/0261807 A1 | 10/2012 | Itoh et al. |
| 2012/0315388 A1 | 12/2012 | Burckhardt et al. |
| 2013/0281580 A1 | 10/2013 | Malofsky et al. |
| 2013/0303719 A1* | 11/2013 | Malofsky ............... C08F 122/14 526/335 |
| 2014/0058031 A1 | 2/2014 | Overbeek et al. |
| 2014/0173889 A1 | 6/2014 | Johnson et al. |
| 2014/0248485 A1 | 9/2014 | Malofsky et al. |
| 2014/0275400 A1 | 9/2014 | Chen et al. |
| 2014/0288230 A1 | 9/2014 | Malofsky et al. |
| 2014/0329980 A1 | 11/2014 | Malofsky et al. |
| 2015/0056879 A1 | 2/2015 | Malofsky et al. |
| 2015/0104660 A1 | 4/2015 | Malofsky et al. |
| 2015/0148480 A1 | 5/2015 | Ellison et al. |
| 2015/0210894 A1 | 7/2015 | Malofsky et al. |
| 2015/0303122 A1 | 10/2015 | Malofsky et al. |
| 2015/0361283 A1 | 12/2015 | Malofsky et al. |

FOREIGN PATENT DOCUMENTS

| | | | |
|---|---|---|---|
| FR | 2788516 A1 | 7/2000 |
| GB | 432628 | 7/1935 |
| GB | 965676 | 8/1964 |
| GB | 965767 | 8/1964 |
| GB | 975733 | 11/1964 |
| JP | S5681537 A | 7/1981 |
| JP | 02-281013 | 11/1990 |
| JP | H08231564 | 9/1996 |
| JP | 09258448 A | 10/1997 |
| JP | 200019936 | 7/2000 |
| JP | 2004-304125 A | 10/2004 |
| JP | 2008174494 | 1/2007 |
| JP | 2011-025247 A | 2/2011 |
| WO | 1999/046619 | 9/1999 |
| WO | WO 99/46619 * | 9/1999 ............... G02B 6/12 |
| WO | 99/055394 | 11/1999 |
| WO | 2006-098514 A1 | 9/2006 |
| WO | 2007/120630 | 10/2007 |
| WO | 2010/129068 A1 | 11/2010 |
| WO | 2011/059104 | 12/2011 |
| WO | 2011/161045 | 12/2011 |
| WO | 2012/054616 A2 | 4/2012 |
| WO | 2012/054633 A2 | 4/2012 |
| WO | 2013059473 A2 | 4/2013 |
| WO | 2013/066629 | 5/2013 |
| WO | 2013/149173 A1 | 10/2013 |
| WO | 2013149165 A1 | 10/2013 |
| WO | 2013149168 A1 | 10/2013 |

OTHER PUBLICATIONS

International Search Report (ISR) and Written Opinion of the Searching Authority in App No. PCT/US2016/027099 dated Jul. 15, 2016, 8 pages in its entirety.

(56) References Cited

OTHER PUBLICATIONS

International Preliminary Report on Patentability in App No. PCT/US2013/070355 dated May 19, 2015, 6 pages in its entirety.
U.S. Appl. No. 14/948,734, filed Nov. 23, 2015.
U.S. Appl. No. 15/094,705, filed Apr. 8, 2016.
Bachman et al.: "Diethyl methylenemalonate", May 17, 1939, Eastman Kodak Company, pp. 493-501.
P. Breton et al., "New Poly(Methylidene Malonate 2.1.2) Nanoparticles: Recent Developments", Targeting of Drugs 4, NATO ASI Series, vol. 273, pp. 161-172, 1994.
Limouzin et al., "Anionic Polymerization of n-Butyl Cyanoacrylate in Emulsion and Miniemulsion" Macromolecules, vol. 36, 2003, pp. 667-674.
"Knoevenagel reaction on a molecular sieve", Li Qifang et al., Chinese Science Bulletin, vol. 12, pp. 914-917.
"Knoevenagel Condensation Over Acidic Zeolite", Zuo Bojun et al., Chinese Journal of Catalysis, vol. 23 (6), pp. 555-558.
"Comparison of the catalytic activity of MOFs and zeolites in Knoevenagel condensation", Maksym Opanasenko, et al., Catalysis Science & Technology, vol. 3 p. 500-507.
Corey et al. "Total Synthesis of Gibberellic Acid. A Simple Synthesiss of a Key Intermediate", J. Am. Chem. Soc. 1982, 104, 6129-6130.
Krishna et al. "Stereodefined Access to 3-Deoxy Sugars Through a Tandem Baylis-Hillman and Lewis Acid Catalyzed Reaction Sequence", European Journal of Organic Chemistry, 2010, 813-817.
International Preliminary Report on Patentability in App No. PCT/US2013/070355 dated May 19, 2015.
M. McCoy, "A New Way to Stick" Chemical & Engineering News, vol. 26, Issue 26 (Jun. 30, 2014), pp. 17-18.
International Search Report (ISR) and Written Opinion of the Searching Authority in App No. PCT/US2015/047445 dated Nov. 30, 2015.
International Search Report (ISR) and Written Opinion of the Searching Authority in App No. PCT/US2015/047466 dated Dec. 1, 2015.
International Search Report (ISR) and Written Opinion of the Searching Authority in App No. PCT/US2015/048846 dated Dec. 4, 2015.
European Search Report of the European Patent Office, Issued in European Application No. 13770173.6-1301 / 2831124; dated Oct. 9, 2015; 7 pages.
Vi. Ware et al.: "DBU: An Efficient Catalyst for Knoeveganel Condensation under Solvent-free Condition," Bulletin of the Catalysis Society of India, (2007), vol. 6, pp. 104-106.
V. G. Nenajdenko et al.: "Reaction of 2-Methylene-1 ,3-Dicarbonyl Compounds Containing a CF3-Group with 1 ,3-Dienes," Tetrahedron, (2000), vol. 56, pp. 6549-6556.
J. S. Yadav et al.: "Phosphane-Catalyzed Knoevenagel Condensation: a Facile Synthesis of a-Cyanoacrylates and a-Cyanoacrylonitriles," Eur. J. Orq. Chem. (2004), pp. 546-551.
B. C. Ranu et al.: "Ionic Liquid as Catalyst and Reaction Medium—a Simple, Efficient and Green Procedure for Knoevenagel Condensation of Aliphatic and Aromatic Carbonyl Compounds Using a Task-Specific Basic Ionic Liquid," Euro. J. Org. Chem., (2006), pp. 3767-3770.
H. A. Oskooie et al.: "On Water: an Efficient Knoevenagel Condensation using 12-Tungstophosphoric Acid as a Reusable Green Catalyst," Synthetic Communications, (2006), vol. 36, pp. 2819-2823.
H. Jiang et al.: "Inorganic Zinc Salts Catalyzed Knoevenagel Condensation at Room Temperature without Solvent," Preparative Biochemistry & Biotechnology, (2009), vol. 39, pp. 194-200.
B. M. Reddy et al.: "An Easy-to-use Heterogeneous Promoted Zirconia Catalyst for Knoevenagel Condensation in liquid Phase under Solvent-Free conditions," Journal of Molecular Catalysis A: Chemical, (2006), vol. 258, pp. 302-307.
D. H. Jung et al.: "New and General Methods for the Synthesis of Arylmethylene Bis(3- Hydroxy-2-Cyclohexene-1-0nes) and Xanthenediones by EDDA and In(OTf)3-Catalyzed One-Pot Domino Knoevenagel/Michael or Koevenagel/Michael/Cyclodehydration Reactions," Bull. Korean Chem. Soc. (2009) vol. 30, No. 9, pp. 1989-1995.
P. Klemarczyk: "Adhesion Studies of Mixtures of Ethyl Cyanoacrylate with a Difunctional Cyanoacrylate Monomer and with other Electron-deficient Olefins," J. Adhesion, (1999), vol. 69, pp. 293-306.
p. Klemarwczyk: "A General Synthesis of 1,1 Disubstituted Electron Deficient Olefins and their Polymer Properties," Polymer, (1998), vol. 39, No. 1, pp. 173-181.
Gill, Charansingh, et al. "Knoevenagel condensation in neutral media: A simple and efficient protocol for the synthesis of electrophillic alkenes catalyzed by anhydrous ferric sulphate with remarkable reusability." Bulletin of the Catalysis Society of India 7 (2008): 153-157.
P. Ballesteros et al.: "DI-tert-Butyl Methylenemalonate [Propanedioic Acid, Methylene-, bis(1, 1-dimethylethyl)ester]," Organic Syntheses. Coil. (1990), vol. 7, p. 142 ; (1986) vol. 64, p. 63.
A. M. Vetrova et al.: "Improvement of the Thermal Stability of Cyanoacrylate Adhesives,"Polymer Science, Series D, (2009), vol. 2, No. 1, pp. 27-30.
A. C. Cope: "Condensation Reactions. I. The Condensation of Ketones with Cyanoacetic Esters and the Mechanism of the Knoevenagel Reaction," Condensation of Ketones with Cyanoacetic Esters, (1937), vol. 59, pp. 2327-2330.
G. Lai et al.: "Ionic Liquid Functionalized Silica Gel: Novel Catalyst and Fixed Solvent,"Tetrahedron Letters (2006), vol. 47, pp. 6951-6953.
J. R. Harjani et al.: "Lewis Acidic Ionic Liquids for the Synthesis of Electrophilic Alkenes via the Knoevenagel condensation," Tetrahedron Letters, (2002), vol. 43, pp. 1127-1130.
P. Ballesteros et al.: "Synthesis of DI-tert-Butyl Methylenemalonate, a Sterically Hindered 1,1-Dicarbonyl Alkene," J. Org. Chem, (1983), vol. 48, pp. 3603-3605.
T. Doi et al.: "Synthesis of Dimethyl gloiosiphne A by Way of Palladium-Catalyzed Domino Cyclization," J. Org. Chem., (2007), vol. 72, pp. 3667-3671.
Takagi et al.: Kogyo Kagaku Zasshi, Reaction of Active Methylene Radicals with Formaldehyde. L. Synthesis of Diethyl Methylenemalonate, 1953, 56, pp. 901-903, English abstract.
McNab, Kirk-Othmer Encyclopedia of chemical Technology, Pyrolysis, Flash Vacuum, 2009, John Wiley & Sons, Inc., pp. 1-26.
Block, "Diethyl bis (hydroxymethyl) malonate "Organic Syntheses, 1973, Coll. vol. 5, p. 381 [vol. 40, p. 27 (1960); Retrieved on Apr. 4, 2014 from internet: http://www.Orgsyn.org/content/pdfs/procedures/cv5p0381.pdf] p. 381, para 1. 1781-026 WO.
Magdalini Matziari et al. "Active methylene phosphinic peptides: a new diversification approach", Organic Letters., vol. 8, No. 11, 2006, pp. 2317-2319, USACS, Washington DC, ISSN: 1523-7060.
Zaragoza Dorwald, Side Reactions in Organic Synthesis, 2005, Wiley-VCH Verlag GmbH & Co., KgaA, Weinheim, Preface. p. IX.
K. Okamura and T. Date, A Facile Conversion of Ethoxydihydropyrans to 4-Cyanoethylisoxazoles, J. Heterocyclic Chem. 33, 383 (1996).
Valentine G. Nenajdenko et al, Reaction of 2-Methylene-1,3-dicarbonyl Compounds Containing a CF3-Group with 1,3-Dienes Tetrahedron 56 (2000) 6549-6556.
Yamauchi et al. "Reactivity of 2-metheyene-1,3-dicarbonyl compounds: catalytic enantioselective Diels-Alder reaction", Tetrahedron Asymetry 12, (2001), 3113-3118.
Cristoph Schotes et al. "Cu(I)- and C(II)- Catalyzed Cyclo- and Michael Addition Reactions of Unsaturated [bet]-Ketoesters" The Journal of Organic Chemistry, vol. 76, No. 14 dated Jul. 15, 2011 p. 5862-5866.
Alejandro Bugarin et al. "Efficient direct [alpha]-methylenation of carbonyls mediated by dissopropylammonium trifluoroacetate", Chemical Communications, vol. 46, No. 10 dated Jan. 1, 2010.
H. Hoffman et al. "Preparation and Selected Reaction of tery-Butyl 2-Methylene-3-oxoalkanoates" Chem. Ber., vol. 124 dated Jan. 1, 1991, pp. 2475-2480.

(56) References Cited

OTHER PUBLICATIONS

M. Yamauchi et al. "Reactivity of 2-Methylene-1, 3-dicarbonyl Compounds. 1,3-Dipolar Cycloaddition Reaction with Ethyl Diazoacetate", Chem. Pham. Bull., vol. 49, No. 12, dated Jan. 1, 2001, pp. 1638-1639.
Lawrence N J et al. "Reaction of Baylis-Hillman products with Swern and Dess-Martin oxidants", Tetrahedron Letters, Pergamon, GB, vol. 42 No. 23 dated Jun. 4, 2001, pp. 3939-3941.
Juliana Vale et al. "Efficient [alpha]-Methylenation of Carbonyl Compounds in Ionic Liquids at Room Temperature", SYNLETT, vol. 2009, No. 01, Jan. 1, 2009 (Jan. 1, 2009), pp. 75-78, XP055170349, ISSN: 0936-5214, DOI: 10.1055/s-0028-1087389 *table 2; compound 3 *.
Weiss et al. Miniemulsion Polymerization as a Means to Encapsulate Organic and Inorganic Materials, Adv. Polymer Science, 2010, pp. 1-52, DOI:10.1007/12_2010_61.
Bhatia, Encapsulation of Particles Using Brittle Subterranean Applications, Thesis submitted to College of Engineering and Mineral Resources at West Virginia University in partial fulfillment of the requirements for the degree of Master of Science in Chemical Engineering, 1999.
McFarland et al, Free Radical Frontal Polymerization with a Microencapsulated Initiator, Macromolecules 2004, vol. 37, pp. 6670-6672.
International Search Report (ISR) and Written Opinion of the Searching Authority in App. No. PCT/US2014/011068 dated May 12, 2014.
International Search Report (ISR) and Written Opinion of the Searching Authority in App. No. PCT/US2011/056903 dated Jun. 7, 2012.
International Search Report (ISR) and Written Opinion of the Searching Authority in App. No. PCT/US2011/056926 dated Feb. 28, 2012.
International Search Report (ISR) and Written Opinion of the Searching Authority in App. No. PCT/US2012/060830 dated Feb. 1, 2013.
International Search Report (ISR) and Written Opinion of the Searching Authority in App. No. PCT/US2012/060840 dated Mar. 12, 2013.
International Search Report (ISR) and Written Opinion of the Searching Authority in App. No. PCT/US2012/060837 dated Jan. 9, 2013.
International Search Report (ISR) and Written Opinion of the Searching Authority in App. No. PCT/US2013/034636 dated Jun. 20, 2013.
International Search Report (ISR) and Written Opinion of the Searching Authority in App. No. PCT/US2013/034641 dated Jun. 25, 2013.
International Search Report (ISR) and Written Opinion of the Searching Authority in App. No. PCT/US2013/034649 dated Aug. 27, 2013.
International Search Report (ISR) and Written Opinion of the Searching Authority in App. No. PCT/US2013/043711 dated Nov. 22, 2013.
International Search Report (ISR) and Written Opinion of the Searching Authority in App. No. PCT/US2013/070355 dated Mar. 19, 2014.
International Search Report (ISR) and Written Opinion of the Searching Authority in App. No. PCT/US2013/072203 dated Apr. 18, 2014.
European Search Report of the European Patent Office, Issued in European Application No. 13767993.2-1302 / 2831185; dated Jan. 7, 2016; 14 pages.

* cited by examiner

Raman Measurements of Polymer
Raman spectrum was taken at 532nm on a JY 64000 Raman Microprobe system.

Infrared Vibrational Spectra

Polymer UV-VIS-NIR Absorption Spectra – 0.18mm thick (7 mil)

UVVISNIR Scaled for Small Absorbance Beyond UV

Visible Wavelengths Absorbance

Telecommunications Wavelengths Absorbance

Comparison of UV/VIS/NIR Spectrum of Exemplary Polymer with common optical film polymers.

Notes: Transparency windows for PET, PC and PM. The step in the PM near 850nm is the grating change in the spectrometer.

Notes: In terms of NIR transmission, the polymers compared in this initial study all being organic, have similar vibrations and similar IR absorptions therefore similar peaks. The BioPM (exemplary polymer) at 3000 nm has a particular nice window for devices of interest that operate in this region.

OPTICAL MATERIAL AND ARTICLES FORMED THEREFROM

CROSS REFERENCE TO RELATED APPLICATIONS

This application is the United States national phase filing under 35 U.S.C. 371 of the corresponding international application number PCT/US2013/043711, filed May 31, 2013, and claims the priority benefit of U.S. Provisional Patent Application No. 61/654,586 filed Jun. 1, 2012 entitled Optical Material and Articles Formed Therefrom and U.S. Provisional Patent Application No. 61/693,626 filed Aug. 27, 2012 entitled Optical Material and Articles Formed Therefrom, each of which is incorporated by reference herein in its respective entirely.

BACKGROUND OF THE INVENTION

1. Field of the Invention

Exemplary embodiments disclosed herein relate to oligomers and polymers and polymerizable compositions useful as optical materials and articles formed therefrom. As used herein, the term "optical materials" refers generally to substances which function to transmit, alter or control electromagnetic radiation in vacuum ultraviolet, ultraviolet, visible, near infrared, infrared, far infrared, and terahertz spectral regions. Optical materials may be articles that utilize the optical properties of the optical materials. Such articles may include monolithic or laminated structures, coatings, adhesives, fibers, faceplates, optical disks, filters, lenses, solar cell components, and LED optics components, to name a few.

Optical properties of interest may include transparency or transmission of radiation at the wavelength(s) of interest, refractive index, birefringence, dispersion, optical anisotropy, polarization, color stability, reflective or anti-reflective characteristics and the like, and the spectral dependency of such properties.

Additionally, certain other physical or chemical properties may be of interest in applications using optical materials. Some properties of interest include chemical (e.g., solvent) resistance, heat resistance, film-forming ability, fiber-forming ability, ease of polymerization, flexibility, gas barrier properties, surface flatness, geometrical stability, impact resistance, scratch and abrasion resistance, toughness, shrinkage, coefficient of thermal expansion, resistance to yellowing, dielectric constant, and the like.

2. Background

Historically, it has been known to use glass or transparent polymer materials such as polymethyl methacrylate (PMMA) and polycarbonate (PC). Although PMMA has excellent optical properties, its use may be limited because of low heat resistance resulting from a glass transition temperature ($T_g$) of about 100° C. PC, on the other hand, has a higher $T_g$ (140° C.) but has poorer optical characteristics when compared to PMMA. Additionally, PC may exhibit low surface hardness causing susceptibility to scratching, low weatherability, and low moldability.

Certain co-inventors of the instant application are also inventors of the subject matter disclosed in published patent applications on improved methods of synthesis of methylene malonates, namely, WO 2012/054616 Synthesis of Methylene Malonates Substantially Free of Impurities, and WO 2012/054633 Synthesis of Methylene Malonates Using Rapid Recovery in the Presence of a Heat Transfer Agent. The synthesis procedures provided therein result in improved yields of heretofore-elusive high quality methylene malonates and other polymerizable compositions having the general formula (I):

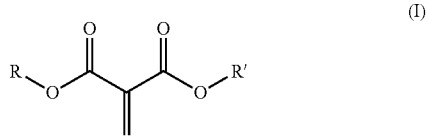

wherein R and R' may be the same or different and may represent nearly any substituent or side-chain.

Certain of these compounds may be amenable to chain-building and/or cross-linking polymerization by anionic or free radical initiation and have the potential to form the basis of a highly valuable and large-scale platform for the chemical synthesis and formulation of new chemical products.

Improvements in the performance of optical materials are continuously sought, especially in the fields of photonics, fiber optics, solar cells, automotive components, optical lenses, displays, windows, architectural glass, optical devices, optical substrates, optical coatings and adhesives. With the advent of improved synthesis processes, opportunities exist for new classes of commercially viable products, in particular, optical materials and their utilization in a variety of applications.

SUMMARY OF THE INVENTION

Exemplary embodiments disclosed herein provide novel and nonobvious improvements in the use of methylene malonate monomers and other polymerizable compositions, or oligomer or polymers derived from the monomeric units as optical materials, articles formed from such compositions or polymers, and methods of utilizing such compositions or polymers. The purpose and advantages of the present invention will be set forth in and apparent from the description that follows.

Exemplary polymerizable compositions include polymerizable di-substituted, di-activated vinyl compositions such as, but not limited to, methylene malonates, methylene β-ketoesters, methylene β-di-ketones, dialkyl disubstituted vinyl, dihaloalkyl disubstituted vinyl, whether monofunctional, difunctional or multifunctional monomeric compositions. Exemplary compositions also include oligomeric or polymeric compositions including repeat units derived from the exemplary monomers. Exemplary articles include, but are not limited to, optical substrates, lenses, films, adhesives, coatings, fibers, fiber cladding, polarizable devices, windows, non-linear optical devices, films, and the like. Certain exemplary embodiments are particularly useful in applications utilizing the UV spectrum, for example, excimer lasers.

In a first aspect of the invention, there is provided an optical material comprising:

an oligomer or polymer material including structural repeat units represented by any of the formulas selected from:

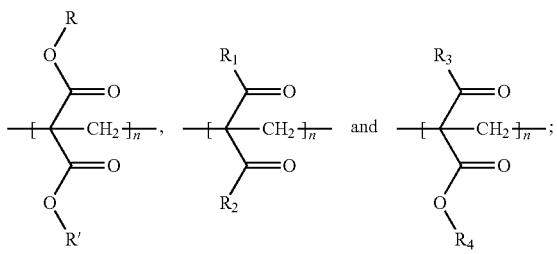

wherein the oligomer or polymer material is formed by curing a polymerizable composition; and wherein, in the selected formula, R and R', $R_1$ and $R_2$, or $R_3$ and $R_4$ are independently selected from the group consisting of $C_1$-$C_{15}$ alkyl, $C_2$-$C_{15}$ alkenyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl-($C_1$-$C_{15}$ alkyl), heteroaryl or heteroaryl-($C_1$-$C_{15}$ alkyl), or alkoxy-($C_{1-15}$ alkyl), each of which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, or ester;

or wherein in the selected formula, R and R', $R_1$ and $R_2$, or $R_3$ and $R_4$ are taken together with the atoms to which they are bound to form a 5-7 membered heterocyclic ring which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, or ester; and wherein the optical material has a low absorbance (≤0.05 absorbance units) or substantially no absorbance (≤0.025 absorbance units) at wavelengths in at least one of the spectral regions selected from: the vacuum UV region (below 200 nm), in the UV region (180 to 360 nm), in the visible region (380-720 nm), in the near IR region (750-2500 nm), in the IR region (2500-1000 nm), the far IR region (>10000 nm) and the terahertz region (about 0.1 to 10 THz).

In an exemplary embodiment, the optical material comprises properties beneficial for optical purposes. For example, the polymerizable composition from which the optical material is formed has a refractive index of between 1.40 and 1.50 measured at 25° C. in a liquid state, prior to polymerization. In an exemplary embodiment, the optical material has a glass transition temperature ($T_g$) of between −30° C. and 100° C. In an exemplary embodiment the optical material exhibits high solvent resistance. In an exemplary embodiment the optical material has a decomposition temperature of at least about 200° C. The optical material may be utilized, for example in optical fibers whether single-mode or multi-mode fibers.

In an exemplary embodiment, the optical material comprises the following formula:

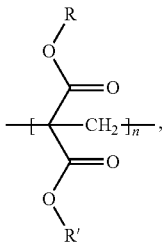

wherein R and R' are independently ethyl or methyl groups; and wherein the optical material has low absorbance or substantially no absorbance of wavelengths in the UV spectral region (180 to 360 nm) or in the visible spectral region (380-720 nm).

In a second aspect of the invention, there is provided an optical component comprising the optical material disclosed herein. The optical component may be an optical waveguide for transmitting electromagnetic radiation selected from IR, UV, or visible radiation. In other exemplary embodiments, the optical component may be a spherical or non-spherical optical lens. In other exemplary embodiments, the optical component may be a substantially transparent architectural article. In other exemplary embodiments, the optical component may be an automotive component. For example, the automotive component may be a headlight lens, a fog light lens, a turn indicator lens, a brake light lens, an illumination cover, and an illumination accessory. In other exemplary embodiments the optical component may comprise a laminated structure wherein at least one layer of the laminated structure comprises the optical material.

In a third aspect of the invention, there is provided an optical material comprising:

a polymerizable material having a formula selected from:

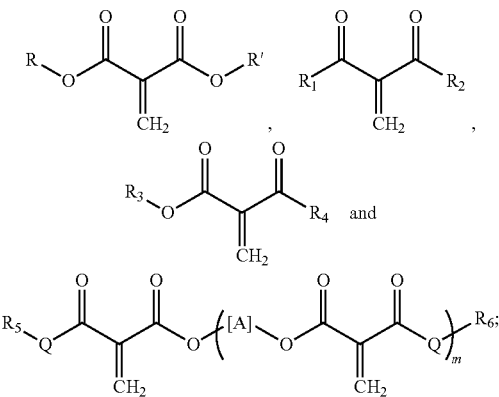

wherein, in the selected formula, R and R', $R_1$ and $R_2$, $R_3$ and $R_4$, and $R_5$ and $R_6$ are independently selected from the group consisting of $C_1$-$C_{15}$ alkyl, $C_2$-$C_{15}$ alkenyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl-($C_1$-$C_{15}$ alkyl), heteroaryl or heteroaryl-($C_1$-$C_{15}$ alkyl), or alkoxy-($C_{1-15}$ alkyl), each of which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, or ester;

or wherein in the selected formula, R and R', $R_1$ and $R_2$, or $R_3$ and $R_4$ are taken together with the atoms to which they are bound to form a 5-7 membered heterocyclic ring which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, or ester;

or wherein in the selected formula -[A]- represents —($CR^A R^B$)$_n$—, —($CR^A R^B$)$_n$—O(C═O)—($CH_2$)$_{1-15}$—(C═O)O—($CR^A R^B$)$_n$—, —($CH_2$)$_n$—[CY]—($CH_2$)$_n$—, a polybutadienyl linking group, a polyethylene glycol linking group, a polyether linking group, a polyurethane linking group, an epoxy linking group, a polyacrylic linking group, or a polycarbonate linking group;

wherein each instance of $R^A$ or $R^B$ is independently H, $C_1$-$C_{15}$ alkyl, $C_2$-$C_{15}$ alkenyl, a moiety represented by the formula:

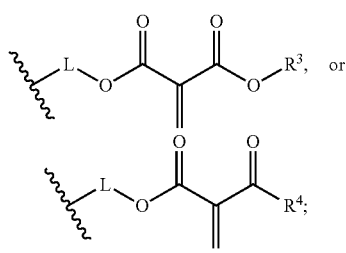

wherein -L- is a linking group selected from the group consisting of alkylene, alkenylene, haloalkylene, cycloalkylene, cycloalkylene, heterocyclylene, heterocyclyl alkylene, aryl-alkylene, heteroarylene or heteroaryl-(alkylene), or alkoxy-(alkylene), each of which may be optionally branched and each of which may be optionally substituted by alkyl, haloalkyl, cycloalkyl, halo cycloalkyl, heterocyclyl, heterocyclyl-(alkyl), aryl, aryl-(alkyl), heteroaryl, $C_1$-$C_{15}$ alkoxy, $C_1$-$C_{15}$ alkylthio, hydroxyl, nitro, azido, cyano, acyloxy, carboxy, ester, each of which may be optionally branched;

$R^3$ is independently selected from the group defined in $R_6$ above; and $R^4$ is alkyl, alkenyl, haloalkyl, cycloalkyl, halo cycloalkyl, heterocyclyl, heterocyclyl alkyl), aryl-(alkyl), heteroaryl or heteroaryl-(alkyl), or alkoxy-(alkyl), each of which may be optionally branched and each of which may be optionally substituted by alkyl, haloalkyl), cycloalkyl, halo cycloalkyl, heterocyclyl, heterocyclyl-(alkyl), aryl, aryl-(alkyl), heteroaryl, $C_1$-$C_{15}$ alkoxy, $C_1$-$C_{15}$ alkylthio, hydroxyl, nitro, azido, cyano, acyloxy, carboxy, ester, each of which may be optionally branched;

—[CY]— represents an alkyl, alkenyl, haloalkyl, cycloalkyl, halo cycloalkyl, heterocyclyl, heterocyclyl alkyl), aryl-(alkyl), heteroaryl or heteroaryl-(alkyl), or alkoxy-(alkyl) group n is an integer from 1 to 25;

m is an integer from 1 to 25;

each instance of Q represents —O— or a direct bond;

and wherein the polymerizable composition has a refractive index of between 1.40 and 1.50 measured at 25° C. in a liquid state, prior to curing.

In a fourth aspect of the invention, there is provided an optical material useful as an optical adhesive. The optical adhesive may be used for bonding first and second substrates of an optical component. In the bonding method, the polymerizable optical material is polymerized to form a bond between the first and second substrates. In certain exemplary embodiments, the optical adhesive polymerizes at ambient temperature. In certain exemplary embodiments, the first and second substrates comprise optical fibers. In certain exemplary embodiments, the first substrate comprises an optical fiber and the second substrate comprises a support member for the optical fiber.

In a fifth aspect of the invention, there is provided an optical device comprising first and second optical fibers and a polymerizable optical adhesive disposed between ends of the first and second optical fibers. After polymerization, the first and second optical fibers are adhered such that an optical signal can pass from the first fiber to the second fiber through the polymerized adhesive without substantial signal loss.

In a sixth aspect of the invention, there is provided a refractive index-matching material comprising any of the optical materials as disclosed herein.

In a seventh aspect of the invention, there is provided a method of repairing an optical fiber comprising: pre-placing ends of optical fibers requiring splicing into a supported arrangement with a polymerizable refractive index-matching material between the ends of the optical fibers; polymerizing the refractive index-matching material to form a splice having optical characteristics substantially corresponding to those of the optical fibers. In an exemplary embodiment, the optical fibers include circumferentially disposed cladding and wherein the ends of the optical fiber to be spliced retain the cladding during the step of polymerizing the refractive index-matching material.

In an eighth aspect of the invention, there is provide an optical composite article comprising first and second optical materials, wherein the first optical material comprises reinforcing or filler members and the second optical material comprises a binder or polymeric matrix.

FIGURES

Certain polymers and oligomers were formed from polymerizable compositions as disclosed herein. Certain optical and spectroscopic properties were obtained as set forth in the following FIGS. 1-8. Visible, IR and Raman spectra were obtained. Differential Scanning calorimetry revealed a melting point near 250 C. Further, comparisons were made of an exemplary polymer with known optical film polymers.

DESCRIPTION OF THE INVENTION

Definitions

Unless defined otherwise, all technical and scientific terms used herein have the meaning commonly understood by a person skilled in the art to which this invention belongs. As used herein, the following terms have the meanings ascribed to them below, unless specified otherwise.

As used herein, the term "beta-dicarbonyl" refers to a compound having the general formula $R_1$—C(O)—CH2-C(O)—$R_2$.

As used herein, the term "exo-methylene derivative compound" refers to a compound having the general formula $R_1$—C(O)—C(═CH2)-C(O)—$R_2$.

As used herein, the term "polymerizable composition" refers to a monomeric, oligomeric, or polymeric composition or mixture comprising molecules that are able to be polymerized by chain extension, cross-linking, or both.

As used herein, the term "monofunctional" refers to an addition monomer, for example a methylene malonate, having only one addition polymerizable group.

As used herein, the term "difunctional" refers to an addition polymerizable function containing monomer, oligomer, resin or polymer, with two such addition polymerizable groups, such as two methylene malonate groups.

As used herein, the term "multifunctional" refers to an addition polymerizable function containing monomer, oligomer, resin or polymer, with two or more such addition polymerizable groups, such as two or more methylene malonate groups. Thus, "difunctional" represents a subgroup of "multifunctional."

As used herein, the term "formulation additives" refers to additives included in a formulated system to enhance physical or chemical properties thereof and to provide a desired result. Such formulation additives include, but are not limited to, dyes, pigments, toughening agents, impact modifiers, rheology modifiers, plasticizing agents, thixotropic agents, natural or synthetic rubbers, filler agents, reinforcing agents, thickening agents, opacifiers, inhibitors, fluorescence markers, anti-oxidants, light stabilizers, thermal degradation reducers, thermal resistance conferring agents, surfactants, wetting agents, and stabilizers.

As used herein, "dispersion" is the dependence of refractive index of the material on the wavelength of radiation interacting with the material.

As used herein, ranges of values are interpreted to mean the end points of the ranges, as well as any sub-ranges included therein.

Exemplary Embodiments

Embodiments disclosed herein are not limited to methylene malonate monomers and polymers derived therefrom, but include di-substituted, di-activated vinyl compounds including di-substituted beta dicarbonyl compounds where the functional groups are, in any combination, ester, ketone, carboxylic acid, or aldehyde groups.

Table 1 provided below provides a listing of exemplary polymerizable compounds and their refractive index measured at 25° C. The refractive index of the polymerized material may vary from the measured values. Additionally, the refractive index may be tailored through the use of various formulation additives. In general, the compounds are thin (low viscosity), clear liquids at ambient temperature. The compounds may be polymerized in the presence of a base (anionic polymerization) or through a free-radical mechanism. For certain optical applications as disclosed herein, a substrate may provide the polymerization initiator, for example, a substrate comprising glass.

TABLE 1

Refractive Index (RI) at 25° C.

| Sample No. | Methylene Malonates | Purity, GC/MS | Purity, NMR | RI |
|---|---|---|---|---|
| 1 | Butyl ethyl methylene Malonate | 95% | 91% | 1.44 |
| 2 | butyl methyl methylene malonate | 88% | 90% | 1.44 |
| 3 | butyl methyl methylene malonate | 92% | 94% | 1.44 |
| 4 | Dibutyl methylene malonate | 95% | 91% | 1.40 |
| 5 | Dibutyl methylene malonate | 96% | 91 | 1.44 |
| 6 | Dihexyl methylene malonate | 92% | 86% | 1.45 |
| 7 | Di-isopropyl methylene malonate | 97% | 96% | 1.43 |
| 8 | Di-n-propyl methylene malonate | 93% | 89% | 1.43 |
| 9 | dipentyl methylene malonate | 96% | 96% | 1.44 |
| 10 | ethyl hexyl methylene malonate | 93% | 91% | 1.44 |
| 11 | ethyl pentyl methylene malonate | 97% | 88% | 1.44 |
| 12 | ethyl pentyl methylene malonate | 92% | 83% | 1.44 |
| 13 | ethyl propyl methylene malonate | 97% | 96% | 1.43 |
| 14 | ethyl propyl methylene malonate | 93% | 102% | 1.43 |
| 15 | hexyl methyl methylene malonate | 94% | 89% | 1.44 |
| 16 | hexyl methyl methylene malonate | 95% | 93% | 1.44 |
| 17 | methyl pentyl methylene malonate | 93% | 93% | 1.44 |
| 18 | methyl pentyl methylene malonate | 90% | 88% | 1.44 |
| 19 | methyl propyl methylene malonate | 91% | 99% | 1.43 |
| 20 | methyl propyl methylene malonate | 87% | 95% | 1.43 |
| 21 | diethoxy ethyl methylene malonate | 97% | 92% | 1.45 |
| 22 | ethoxyethyl ethyl methylene malonate | 91% | 90% | 1.44 |
| 23 | ethoxyethyl methyl methylene malonate | 96% | 77% | 1.44 |
| 24 | ethyl ethyl methoxy methylene malonate | 96% | 95% | 1.44 |
| 25 | methoxyethyl methyl methylene malonate | 91% | 95% | 1.44 |
| 26 | methoxyethyl methyl methylene malonate | 92% | 97% | 1.44 |
| 27 | dimethoxy ethyl methylene malonate | 93% | 95% | 1.45 |

The optical and spectroscopic characteristics of certain exemplary polymer samples were obtained, i.e. visible, IR and Raman spectra. The exemplary polymer samples included poly-diethyl methyl methylene malonate (pDEMM). For the samples studied, differential scanning calorimetry revealed a melting point near 250° C. Additionally, reference samples of polyethylene terephthalate (PET) and polycarbonate (PC) were also studied. The data are provided in FIGS. 1-8.

Figure 1:
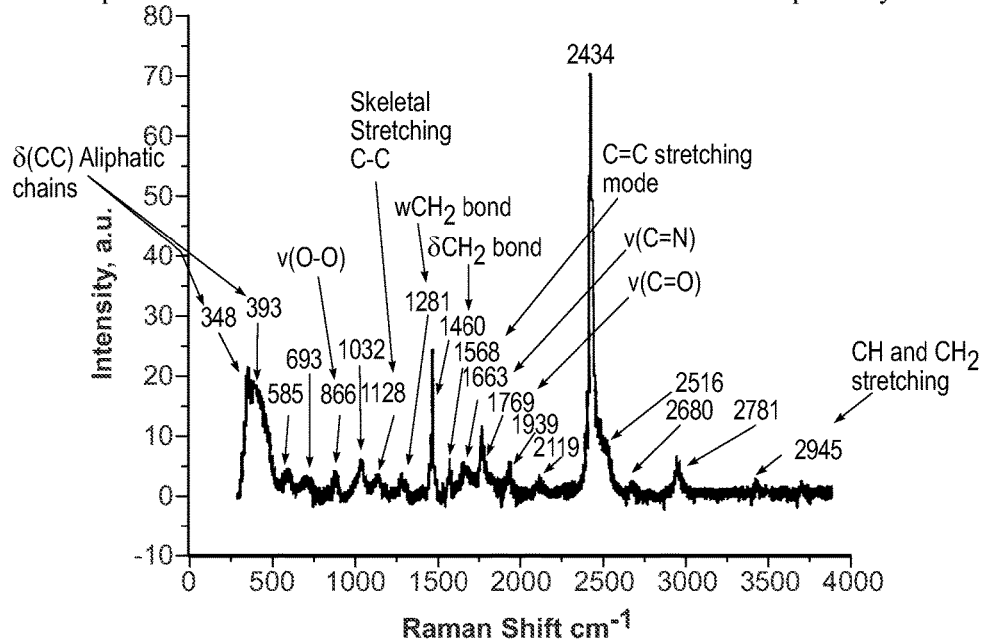
FIG. 1 shows Raman measurements of the exemplary polymer taken at 532 nm on a JY 64000 Raman microprobe system.
Figure 2:
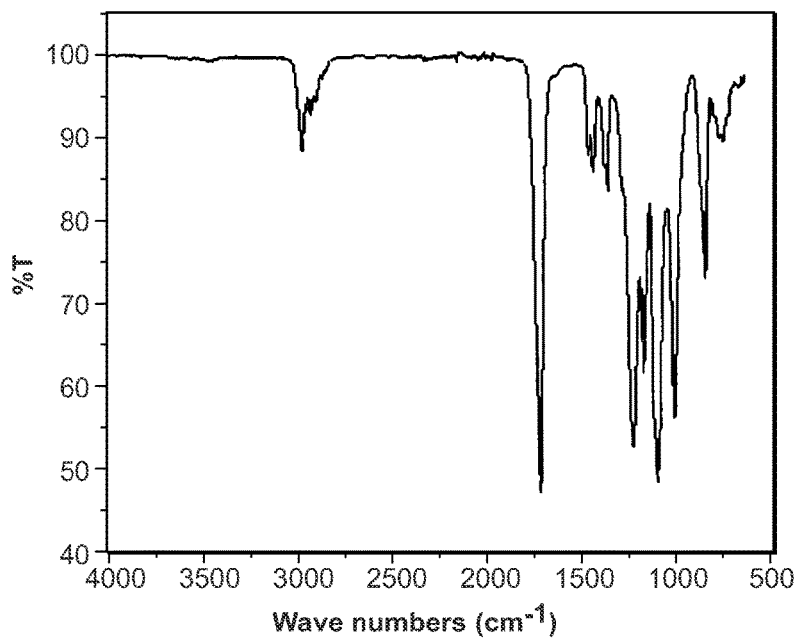
FIG. 2 shows infrared vibrational spectra of the exemplary polymer. As shown, there exists a wide range of wavenumbers where the % transmittance is nearly 100%.
Figure 3:
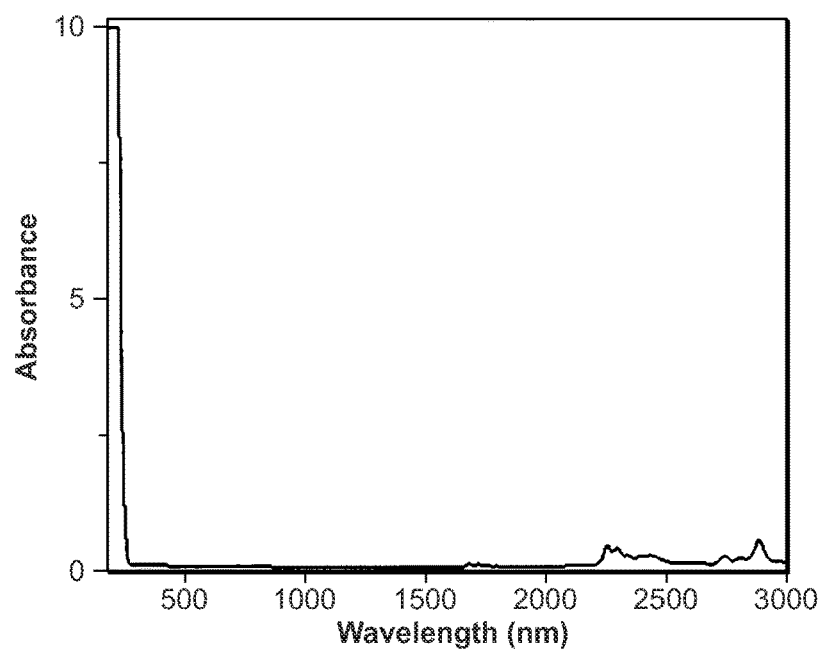
Figure 4:
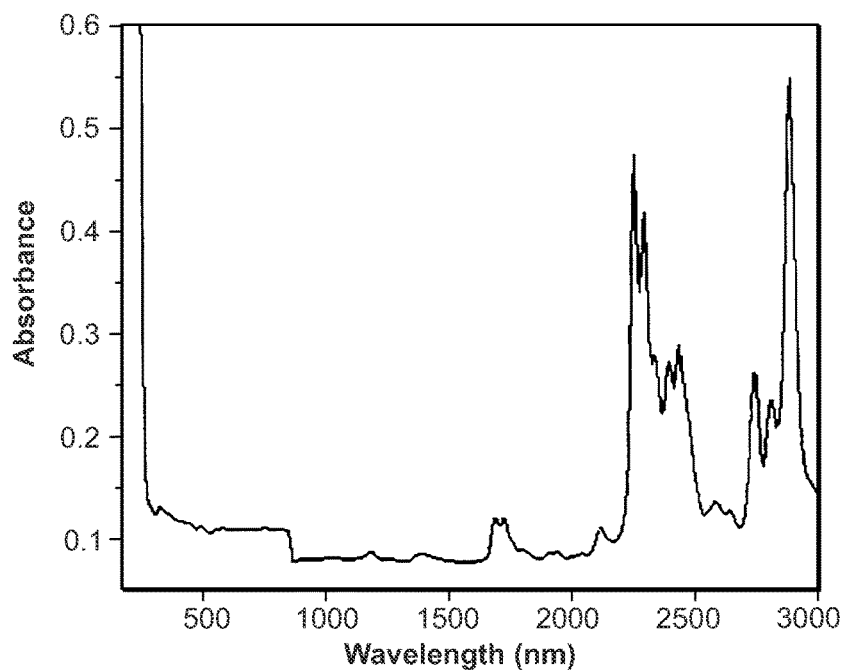

FIG. 3 provides the absorption spectra for the exemplary polymer across the UV0VIS-NIR spectra showing a wide range of wavelengths where the absorbance is very low, and substantially zero in some cases. FIG. 4 provides the absorption spectra with an expanded absorbance scale to show greater detail.

Figure 5:
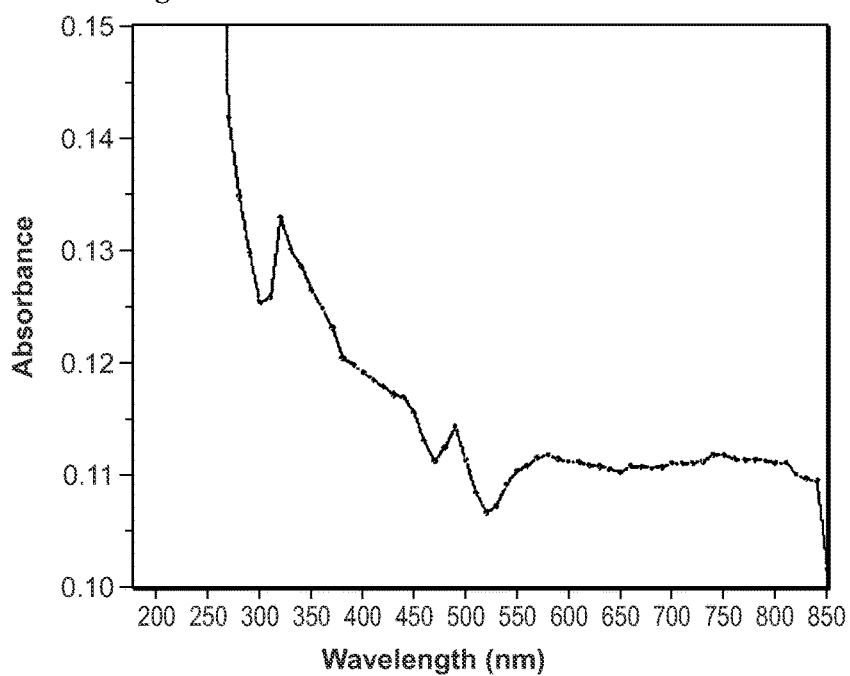

FIG. 5 provides visible wavelengths absorbance showing low absorbance values across the visible light spectrum.

Figure 6:
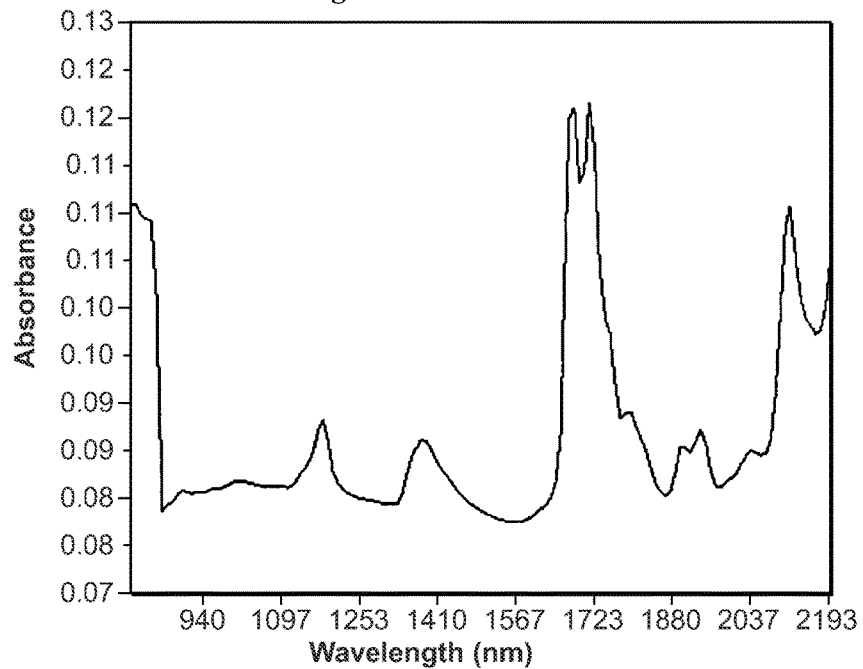

FIG. 6 provides absorbance data across wavelengths of particular interest in telecommunications applications. As shown, there are several windows of opportunity for use of the exemplary optical material in telecommunications as the absorbance is very low.

Figure 7:
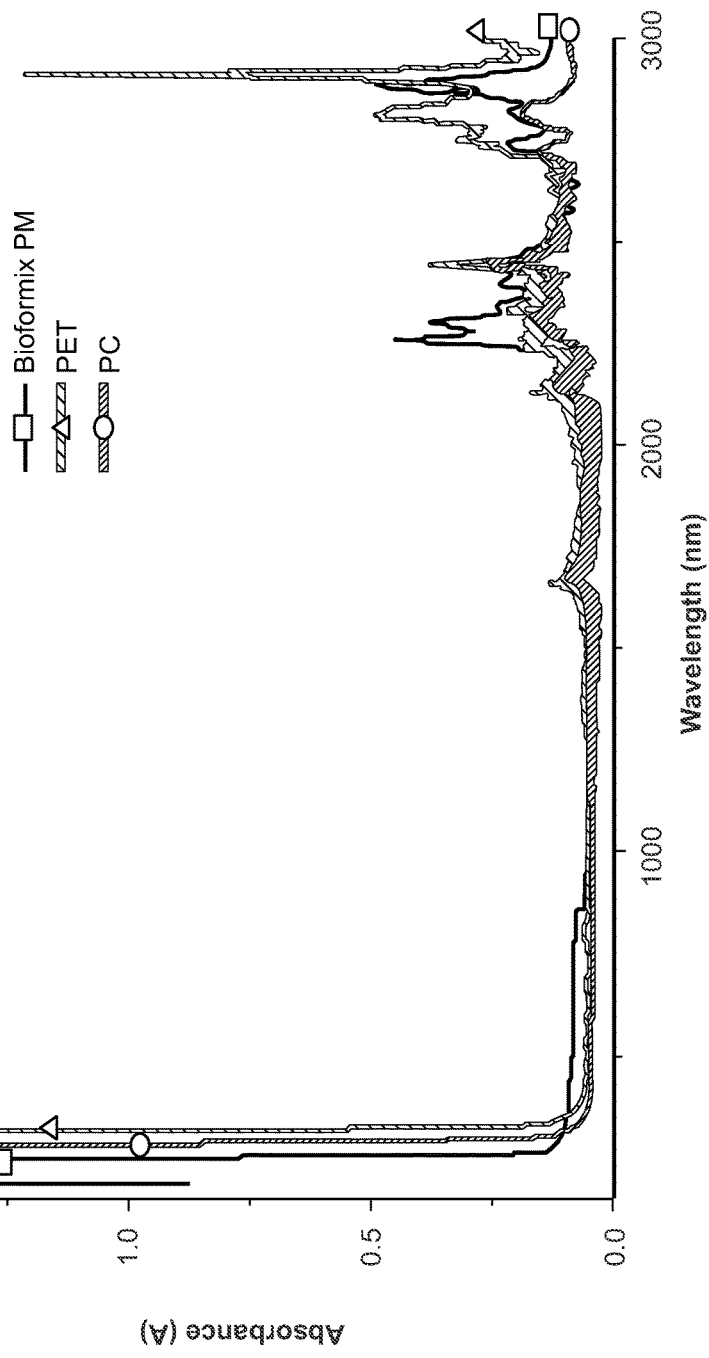

FIG. 7 provides a comparison of UV/VIS/NIR spectra of the exemplary polymer with PET and PC. The step in the exemplary polymer near 850 nm is the grating change in the spectrometer.

Figure 8:
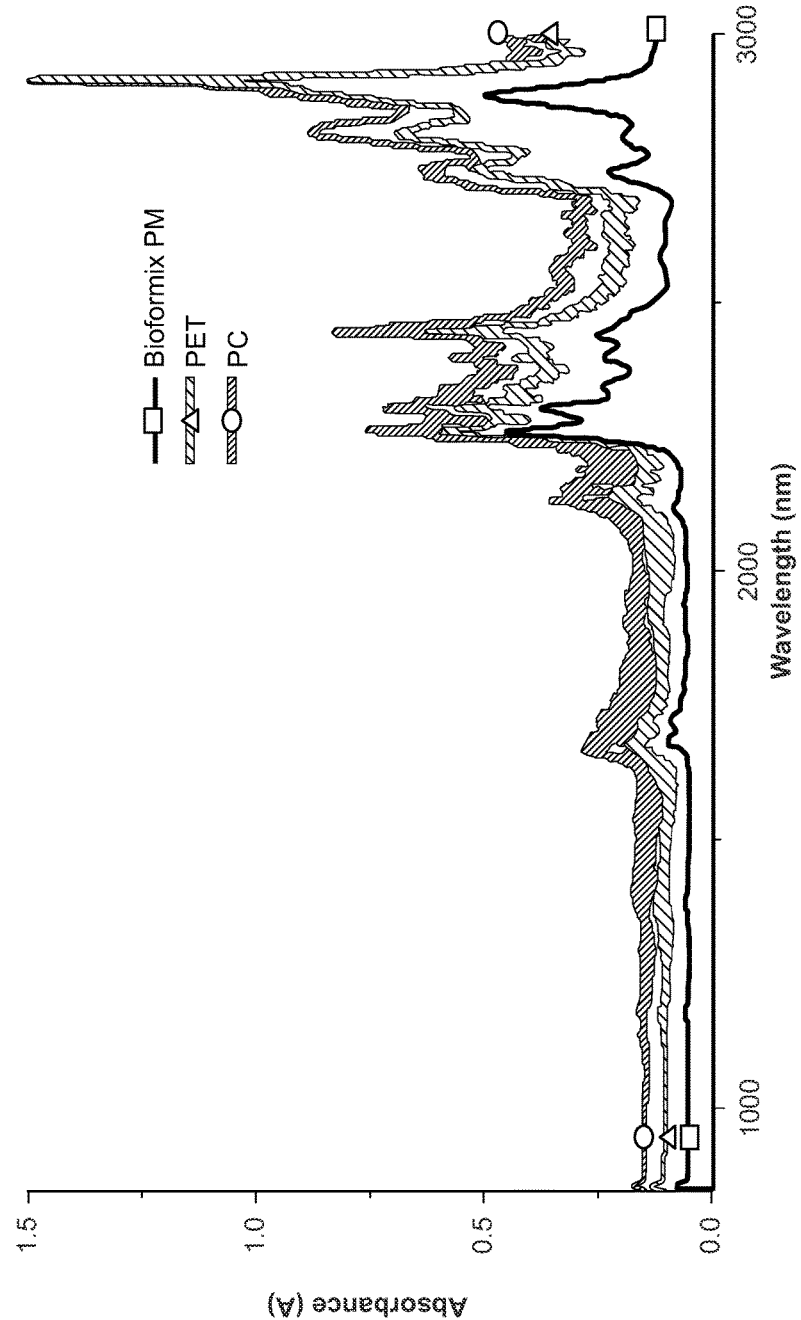

FIG. 8 provides NIR and IR absorption spectra of the exemplary polymer and PET and PC. In terms of NIR transmission, the polymers compared in the study are all organic materials and show similar vibrations and similar IR absorptions. As shown in the figure, the exemplary polymer has a particularly low absorbance window around 3000 nm that can be utilized in optical devices and components that operate in this region.

As the figures indicate, the exemplary polymer possesses desirable optical qualities that can be utilized in a wide variety of optical applications.

The polymerizable compositions as disclosed herein are able to form oligomers and polymers having repeat units as provided below:

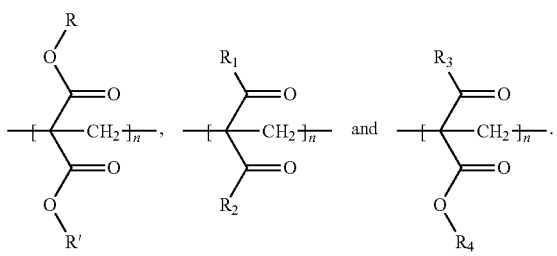

The polymers or oligomers so formed exhibit low or substantially no absorbance of wavelengths in at least one of the spectral regions selected from: the vacuum UV region (below 200 nm), in the UV region (180 to 360 nm), in the visible region (380-720 nm), in the near IR region (750-2500 nm), in the IR region (2500-1000 nm), the far IR region (>10000 nm) and the terahertz region (about 0.1 to 10 THz).

The materials disclosed herein represent a far-reaching platform. Thus in the structures provided herein R and R', $R_1$ and $R_2$, or $R_3$ and $R_4$ are independently selected from the group consisting of C1-C15 alkyl, C2-C15 alkenyl, halo-(C1-C15 alkyl), C3-C6 cycloalkyl, halo-(C3-C6 cycloalkyl), heterocyclyl, heterocyclyl-(C1-C15 alkyl), aryl-(C1-C15 alkyl), heteroaryl or heteroaryl-(C1-C15 alkyl), or alkoxy-(C1-15 alkyl), each of which may be optionally substituted by C1-C15 alkyl, halo-(C1-C15 alkyl), C3-C6 cycloalkyl, halo-(C3-C6 cycloalkyl), heterocyclyl, heterocyclyl-(C1-C15 alkyl), aryl, aryl-(C1-C15 alkyl), heteroaryl, C1-C15 alkoxy, C1-C15 alkylthio, hydroxyl, nitro, azido, cyano, acyloxy, carboxy, or ester;

or wherein in the selected formula, R and R', $R_1$ and $R_2$, or $R_3$ and $R_4$ are taken together with the atoms to which they are bound to form a 5-7 membered heterocyclic ring which may be optionally substituted by C1-C15 alkyl, halo-(C1-C15 alkyl), C3-C6 cycloalkyl, halo-(C3-C6 cycloalkyl), heterocyclyl, heterocyclyl-(C1-C15 alkyl), aryl, aryl-(C1-C15 alkyl), heteroaryl, C1-C15 alkoxy, C1-C15 alkylthio, hydroxyl, nitro, azido, cyano, acyloxy, carboxy, or ester.

The polymerizable composition from which the optical material is formed has a refractive index of between 1.40 and 1.50 measured at 25° C. in a liquid state, prior to polymerization, some examples of which are provided in Table 1. In an exemplary embodiment, the optical material has a glass transition temperature ($T_g$) of between −30° C. and 50° C. In an exemplary embodiment the optical material exhibits high solvent resistance. In an exemplary embodiment the optical material has a decomposition temperature of at least about 200° C.

In an exemplary embodiment, the optical material comprises the following formula:

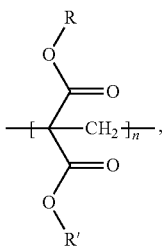

wherein R and R' are independently ethyl or methyl groups; and wherein the optical material has low or substantially no absorbance of wavelengths in the UV spectral region (180 to 360 nm) or in the visible spectral region (380-720 nm).

The optical material disclosed herein may be utilized in providing an optical component. The optical component may be an optical waveform for transmitting electromagnetic radiation selected from IR, UV, or visible radiation. In other exemplary embodiments, the optical component may be a spherical or non-spherical optical lens. In other exemplary embodiments, the optical component may be a substantially transparent architectural article. In other exemplary embodiments, the optical component may be a film. In other exemplary embodiments, the optical component may be an automotive component. For example, the automotive component may be a headlight lens, a fog light lens, a turn indicator lens, a brake light lens, an illumination cover, and an illumination accessory. In other exemplary embodiments the optical component may comprise a laminated structure wherein at least one layer of the laminated structure comprises the optical material.

In other exemplary embodiments, the optical material may comprise the uncured material, for example for use as an optical adhesive or refractive index-matching material.

Exemplary polymerizable materials include:

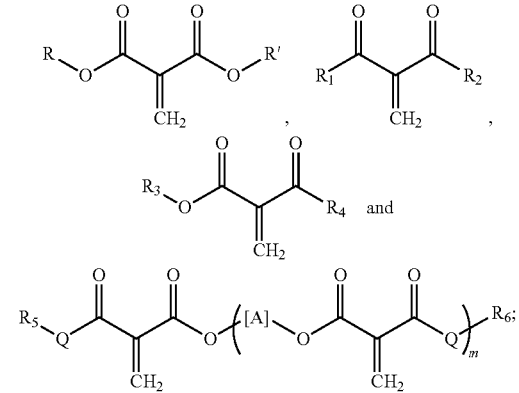

wherein, in the selected formula, R and R', $R_1$ and $R_2$, $R_3$ and $R_4$, and $R_5$ and $R_6$ are independently selected from the group consisting of $C_1$-$C_{15}$ alkyl, $C_2$-$C_{15}$ alkenyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl-($C_1$-$C_{15}$ alkyl), heteroaryl or heteroaryl-($C_1$-$C_{15}$ alkyl), or alkoxy-($C_{1-15}$ alkyl), each of which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, or ester;

or wherein in the selected formula, R and R', $R_1$ and $R_2$, or $R_3$ and $R_4$ are taken together with the atoms to which they are bound to form a 5-7 membered heterocyclic ring which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, or ester; or wherein in the selected formula -[A]- represents —$(CR^A R^B)_n$—, —$(CR^A R^B)_n$—O(C=O)—$(CH_2)_{1-15}$—(C=O)O—$(CR^A R^B)_n$—, —$(CH_2)_n$—[CY]—$(CH_2)_n$, a polybutadienyl linking group, a polyethylene glycol linking group, a polyether linking group, a polyurethane linking group, an epoxy linking group, a polyacrylic linking group, or a polycarbonate linking group;

wherein each instance of $R^A$ or $R^B$ is independently H, $C_1$-$C_{15}$ alkyl, $C_2$-$C_{15}$ alkenyl, a moiety represented by the formula:

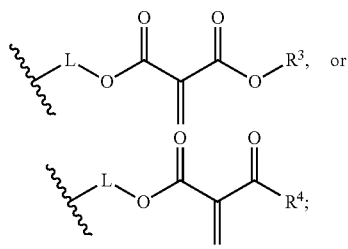

wherein -L- is a linking group selected from the group consisting of alkylene, alkenylene, haloalkylene, cycloalkylene, cycloalkylene, heterocyclylene, heterocyclyl alkylene, aryl-alkylene, heteroarylene or heteroaryl-(alkylene), or alkoxy-(alkylene), each of which may be optionally branched and each of which may be optionally substituted by alkyl, haloalkyl, cycloalkyl, halo cycloalkyl, heterocyclyl, heterocyclyl-(alkyl), aryl, aryl-(alkyl), heteroaryl, $C_1$-$C_{15}$ alkoxy, $C_1$-$C_{15}$ alkylthio, hydroxyl, nitro, azido, cyano, acyloxy, carboxy, ester, each of which may be optionally branched;

$R^3$ is independently selected from the group defined in $R_6$ above; and $R^4$ is alkyl, alkenyl, haloalkyl, cycloalkyl, halo cycloalkyl, heterocyclyl, heterocyclyl alkyl), aryl-(alkyl), heteroaryl or heteroaryl-(alkyl), or alkoxy-(alkyl), each of which may be optionally branched and each of which may be optionally substituted by alkyl, haloalkyl), cycloalkyl, halo cycloalkyl, heterocyclyl, heterocyclyl-(alkyl), aryl, aryl-(alkyl), heteroaryl, $C_1$-$C_{15}$ alkoxy, $C_1$-$C_{15}$ alkylthio, hydroxyl, nitro, azido, cyano, acyloxy, carboxy, ester, each of which may be optionally branched;

—[CY]— represents an alkyl, alkenyl, haloalkyl, cycloalkyl, halo cycloalkyl, heterocyclyl, heterocyclyl alkyl), aryl-(alkyl), heteroaryl or heteroaryl-(alkyl), or alkoxy-(alkyl) group n is an integer from 1 to 25;

m is an integer from 1 to 25;

each instance of Q represents —O— or a direct bond; and wherein the polymerizable composition has a refractive index of between 1.40 and 1.50 measured at 25° C. in a liquid state, prior to curing.

An exemplary optical adhesive may be used for bonding first and second substrates of an optical component. In the bonding method, the polymerizable optical material is polymerized to form a bond between the first and second substrates. In certain exemplary embodiments, the optical adhesive polymerizes at ambient temperature. In certain exemplary embodiments, the first and second substrates comprise optical fibers. In certain exemplary embodiments, the first substrate comprises an optical fiber and the second substrate comprises a support member for the optical fiber. Exemplary support members may be fiber optic connectors that are well known in the art.

An optical device may be provided using principles disclosed herein. For example an optical device may include first and second optical fibers and a polymerizable optical adhesive disposed between ends of the first and second optical fibers. After polymerization of the optical adhesive, the first and second optical fibers are adhered such that an optical signal can pass from the first fiber to the second fiber through the polymerized adhesive without substantial signal loss.

The optical materials disclosed herein (whether polymerized or polymerizable) may be utilized in applications requiring refractive index matching, for example in optical fiber splicing.

An exemplary embodiment of the invention provides a method of repairing or splicing an optical fiber. In the inventive method, the ends of optical fibers requiring splicing are pre-paced into a supported arrangement with a polymerizable refractive index-matching material between the ends of the optical fibers. The refractive index-matching material is thereafter polymerized to form a splice having optical characteristics substantially corresponding to those of the optical fibers. In an exemplary embodiment, the optical fibers include circumferentially disposed cladding and wherein the ends of the optical fiber to be spliced retain the cladding during the step of polymerizing the refractive index-matching material.

In an exemplary embodiment, there is provide an optical composite article comprising first and second optical materials, wherein the first optical material comprises the reinforcing or filler members and the second optical material comprises a binder or polymeric matrix. The reinforcing or filler members may comprise any shape or form as desired, such as fibers, chopped fibers, particles, and the like. Additionally, a first optical material may be the polymer optical material carried in a polymerizable composition comprising the second optical material. Thus, it is possible to provide, for example, a transparent composite material.

In fiber optics and telecommunications, a refractive index-matching material may be used in conjunction with pairs of mated connectors or with mechanical splices to reduce signal reflected in the guided mode. Such materials are used to minimize Fresnel reflections that would otherwise occur at the smooth end faces of a fiber.

Exemplary embodiments disclosed herein provide optical material that is superior in transparency, heat resistance, surface hardness (up to 6H on a pencil hardness test), mechanical strength, and other desired properties.

Polymerization of the optical material disclosed herein may be conducted by any known polymerization process including bulk polymerization, solution polymerization, suspension polymerization, and emulsion polymerization. Additionally, especially for optical adhesives, the optical material may be designed for polymerization on demand when contacting a substrate with sufficient basic sites, e.g., glass fiber.

The optical material may be formulated with formulation additives to provide further desired characteristics. Additionally, exemplary embodiments may be used to provide protective films or anti-reflective/privacy coatings for lap top screens, digital devices and the like.

Thus, exemplary embodiments disclosed herein are useful as optical materials, polymerizable compositions exhibiting desired optical qualities upon cure, and articles and structures comprising the optical materials and/or the polymerizable compositions.

What is claimed is:

1. An optical component comprising an optical material, the optical material comprising:

an oligomer or polymer material comprising structural repeating units represented by any of the formulas selected from:

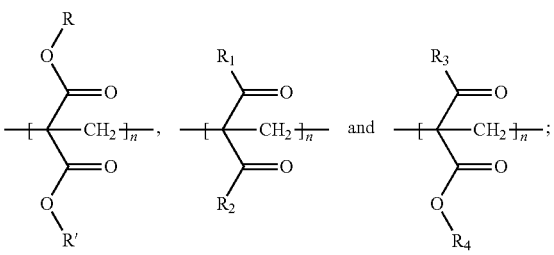

wherein the oligomer or polymer material is formed by curing a polymerizable composition;

wherein, in the selected formula, R and R', $R_1$ and $R_2$, or $R_3$ and $R_4$ are independently selected from the group consisting of $C_1$-$C_{15}$ alkyl, $C_2$-$C_{15}$ alkenyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl-($C_1$-$C_{15}$ alkyl), heteroaryl, heteroaryl-($C_1$-$C_{15}$ alkyl), and alkoxy —($C_1$-$C_{15}$ alkyl), each of which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-($C_1$-$C_{15}$ alkyl), heteroaryl, $C_1$-$C_{15}$ alkoxy, $C_1$-$C_{15}$ alkylthio, hydroxyl, nitro, azido, cyan, acyloxy, carboxy, or ester; or wherein, in the selected formula, R and R', $R_1$ and $R_2$, or $R_3$ and $R_4$ are taken together with the atoms to which they are bound to form a 5-7 membered heterocyclic ring which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, or ester; and wherein the optical material has a low absorbance, or substantially no absorbance, of wavelengths in one or more of the spectral regions including the vacuum ultraviolet region below 200 nm, the ultraviolet region between 180 nm to 360 nm, the visible region between 380 nm to 720 nm, the near infrared region between 750 nm to 2,500 nm, the infrared region between 2,500 nm to 10,000 nm, the far infrared region greater than 10,000 nm and the terahertz region between about 0.1 THz and 10 THz.

2. The optical component according to claim 1, wherein the polymerizable composition has a refractive index between 1.40 and 1.50 when measured at 25° C. in a liquid state, prior to polymerization.

3. The optical component according to claim 1, wherein the optical material comprises a glass transition temperature ($T_g$) between −30° C. and 100° C.

4. The optical component according to claim 1, wherein the optical material exhibits a high solvent resistance.

5. The optical component according to claim 1, wherein the optical material comprises a decomposition temperature of about 200° C. or more.

6. The optical component according to claim 1, wherein structure repeating unit has the formula:

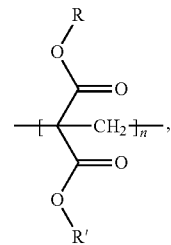

and
wherein R and R' are independently ethyl or methyl groups; and
wherein the optical material has low absorbance, or substantially no absorbance, of wavelengths in the ultraviolet spectral region between 180 nm to 360 nm or the visible spectral region between 380 nm to 720 nm.

7. The optical component of claim 1, which includes one or more of:
an optical waveguide for transmitting electromagnetic radiation selected from the group consisting of infrared, ultraviolet, and visible radiation;
a spherical or non-spherical optical lens;
a substantially transparent architectural article;
an automotive component; and
one or more layers of a laminated structure, wherein at least one layer of the laminated structure comprises the optical material.

8. The optical component according to claim 7, wherein the automotive component is one or more of a headlight lens, a fog light lens, a turn indicator lens, a brake light lens, an illumination cover, or an illumination accessory.

9. An optical composite article comprising at least first and second optical materials according to claim 1, wherein the first optical material comprises reinforcing or filler members and the second optical material comprises a binder or polymeric matrix.

10. An optical fiber comprising the optical material according to claim 1.

11. The optical fiber according to claim 10 is a single-mode fiber or a multi-mode fiber.

* * * * *